United States Patent
Ohashi et al.

(10) Patent No.: US 11,155,879 B2
(45) Date of Patent: Oct. 26, 2021

(54) METHOD OF PREDICTING EFFECTS OF CDC7 INHIBITOR

(71) Applicant: TAKEDA PHARMACEUTICAL COMPANY LIMITED, Osaka (JP)

(72) Inventors: Akihiro Ohashi, Kanagawa (JP); Kenichi Iwai, Kanagawa (JP); Tadahiro Nambu, Kanagawa (JP); Ryo Dairiki, Kanagawa (JP); Yuko Ishii, Cambridge, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 105 days.

(21) Appl. No.: 16/490,143

(22) PCT Filed: Mar. 1, 2017

(86) PCT No.: PCT/JP2017/008206
§ 371 (c)(1),
(2) Date: Aug. 30, 2019

(87) PCT Pub. No.: WO2018/158898
PCT Pub. Date: Sep. 7, 2018

(65) Prior Publication Data
US 2020/0010904 A1   Jan. 9, 2020

(51) Int. Cl.
*C12Q 1/6886* (2018.01)
*A61P 35/00* (2006.01)
*A61K 31/519* (2006.01)

(52) U.S. Cl.
CPC .......... *C12Q 1/6886* (2013.01); *A61K 31/519* (2013.01); *A61P 35/00* (2018.01); *C12Q 2600/106* (2013.01); *C12Q 2600/136* (2013.01); *C12Q 2600/156* (2013.01)

(58) Field of Classification Search
CPC ..... A61K 31/519; A61P 35/00; C12Q 1/6886; C12Q 2600/106; C12Q 2600/136; C12Q 2600/156
See application file for complete search history.

(56) References Cited

U.S. PATENT DOCUMENTS

| 2013/0029969 A1* | 1/2013 | Homma | C07D 495/04 514/210.21 |
| 2014/0135370 A1 | 5/2014 | Vukovic | |
| 2018/0155770 A1* | 6/2018 | Velculescu | C12Q 1/6816 |

FOREIGN PATENT DOCUMENTS

| WO | 2011102399 A1 | 8/2011 |
| WO | 2011112635 A1 | 9/2011 |

OTHER PUBLICATIONS

Bournet et al. (European J of Cancer, 54, 2016, 75-83) (Year: 2016).*
Bonte, et al. "Cdc7-Dbf4 Kinase Overexpression in Multiple Cancers and Tumor Cell Lines is Correlated with P53 Inactivation", Neoplasia, vol. 10, No. 9, Sep. 2008, pp. 920-931.
Jiang, W., et al., "Mammalian Cdc7-Dbf4 protein kinase complex is essential for initiation of DNA replication," EMBO Journal, vol. 18, No. 20 (1999), pp. 5703-5713.
Kim, J.J., et al., "Cdc7 kinase mediates Claspin phosphorylation in DNA replication checkpoint," Oncogene, 27 (2008), pp. 3475-3482.
Masai, H., et al., "Cdc7 Kinase Complex: A Key Regulator in the Initiation of DNA Replication," Journal of Cellular Physiology, 190 (2002), pp. 287-286.
Montagnoli, A., et al., "Cdc7 Inhibition Reveals a p53-Dependent Replication Checkpoint That is Defective in Cancer Cells," Cancer Research, 64, Oct. 1, 2004, pp. 7110-7116.
Skoura, E., et al., "Preclinical research in treatment of pancreatic cancer", Journal of the Pancreas, vol. 14, No. 4, Jul. 1, 2013, pp. 384-387.
Tenca, P., et al., "Cdc7 Is an Active Kinase in Human Cancer Cells Undergoing Replication Stress," Hournal of Biological Chemistry, vol. 282, No. 1, Jan. 5, 2007, pp. 208-215.

* cited by examiner

*Primary Examiner* — Umamaheswari Ramachandran
(74) *Attorney, Agent, or Firm* — Honigman LLP; Lucy X. Yang; Jonathan P. O'Brien

(57) ABSTRACT

The present invention relates to a method of predicting the likelihood that a patient will respond therapeutically to a pancreatic cancer treatment comprising the administration of 2-[(2S)-1-azabicyclo[2.2.2]oct-2-yl]-6-(3-methyl-1H-pyrazol-4-yl)thieno[3,2-d]pyrimidin-4(3H)-one (Compound 1) and/or tautomers thereof or a pharmaceutically acceptable salt or hydrate thereof, comprising the steps of: STEP (1): determining a KRAS gene mutation status of a sample from a patient, and STEP (2): predicting an increased likelihood that the patient will respond therapeutically to the pancreatic cancer treatment if the patient has the presence of KRAS gene mutation(s), and to methods of treating pancreatic cancer.

3 Claims, 1 Drawing Sheet

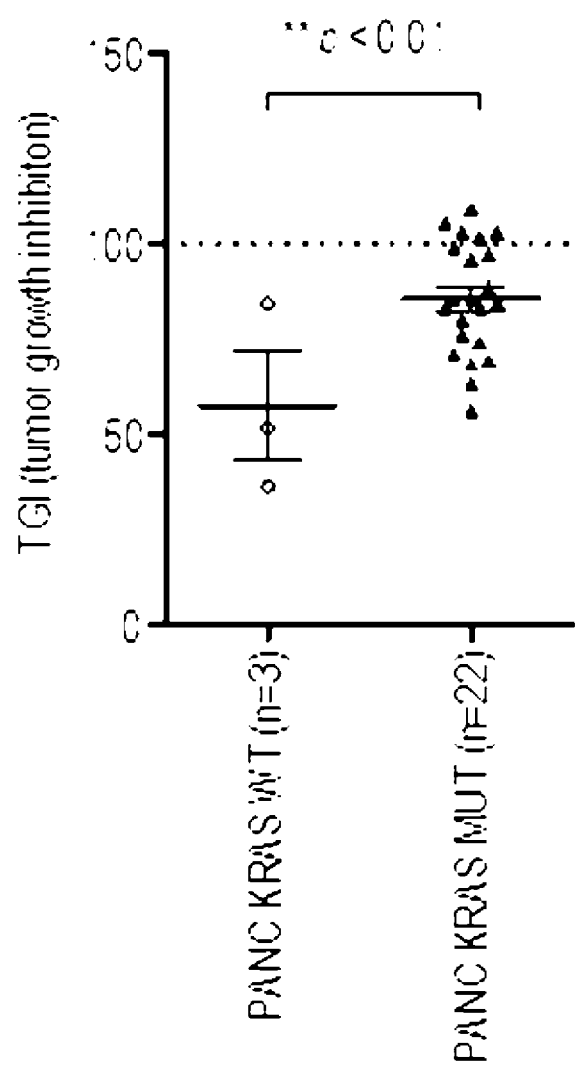

METHOD OF PREDICTING EFFECTS OF CDC7 INHIBITOR

CROSS-REFERENCE TO RELATED APPLICATIONS

This application is a 35 U.S.C. § 371 United States National Phase Application of, and claims priority to, PCT Application No. PCT/JP2017/008206, filed Mar. 1, 2017. The entire contents of the aforesaid application is incorporated by reference herein in its entirety.

TECHNICAL FIELD

The present invention relates to methods which may be useful for predicting effects of a cell division cycle 7 (Cdc7) inhibitor. More particularly, the present invention relates to methods which may be useful for predicting the likelihood that a patient will respond therapeutically to treatment with a Cdc7 inhibitor.

BACKGROUND ART

A characteristic of cancer is an abnormal cell proliferation with a broken control mechanism. Most cancer cells grow more rapidly than cells of normal tissues. In the cell division cycle, chromosome duplication is essential and replication of DNA in S phase is tightly regulated. Inhibition of DNA replication has been confirmed to be an effective therapy for cancer treatment and, for example, DNA replication inhibitors such as hydroxyurea (HU), gemcitabine and active metabolites of 5-fluorouracil, and the like are widely used as therapeutic agents for cancer in clinical practice.

Cdc7 is an evolutionarily well-conserved serine/threonine kinase and plays an important role in the initiation of DNA replication (non-patent document 1). The kinase activity of Cdc7 is controlled by binding with its activating partner. From the late stage of G1 phase to S phase, Cdc7 forms a complex with Dbf4 (also known as ASK) and phosphorylates Cdc7 substrate(s) to control transition from the G1 phase to the S phase (non-patent document 2). Furthermore, recent studies have reported that Cdc7 plays important roles in both DNA replication and DNA damage signaling pathways (non-patent document 3).

In recent years, Cdc7 kinase is receiving attention as an attractive target in cancer treatments. Overexpression of Cdc7 is observed in clinical tumors such as breast cancer, colorectal cancer, lung cancer and the like, and many cancer cell lines (non-patent document 4). In some cancer cell lines, an increase in chromosomal copy number of an activating factor, Dbf4, is found. Interestingly, a cancer cell line and an untransformed fibroblast cell line show different responses to suppression of Cdc7 expression using siRNA. The suppression of Cdc7 expression using siRNA causes the S phase arrest in cancer cell lines and induces apoptosis, whereas in normal cells it induces the G1 phase arrest in a p53 activity-dependent manner (non-patent document 5). Furthermore, Cdc7 kinase is activated in the cells under replication stress, and apoptosis induced by hydroxyurea and etoposide increases in the Cdc7 down-regulated cells (non-patent document 6). Thus, a Cdc7 inhibitor, as a single agent or in combination with other chemotherapeutic agents, is useful for a selective cancer treatment.

Patent document 1 describes a compound which may be useful as a Cdc7 kinase inhibitor, a compound represented by the formula I:

[Chem.1]

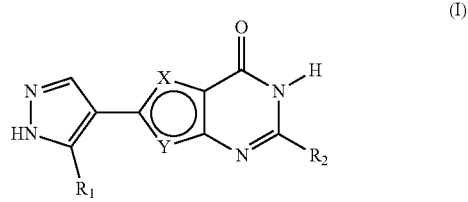

wherein
one of X and Y is a sulfur atom, and the other is CH,
$R_1$ is a $C_{1-6}$ alkyl group optionally substituted by halogen atom(s),
$R_2$ is a substituent,
or a salt thereof.

Patent document 1 describes that the compound of the formula (I) can be used for the prophylaxis or treatment of cancer including hematologic cancer, breast cancer, colorectal cancer, lung cancer, pancreatic cancer and the like.

New prognostic and predictive markers, which may facilitate individualized patient therapy are needed to accurately predict a patient's response to treatments, and in particular, identify the development of resistance to small molecule or biological molecule drugs, in order to identify the best treatment regimens. The problem may be solved by the identification of new parameters that can better predict the patient's sensitivity to treatment. The characterization of patient samples is a crucial aspect of cancer diagnosis and treatment. The association of a patient's response to a treatment with molecular and genetic markers can open up new opportunities for treatment development in non-responding patients, or distinguish a treatment's indication among other treatment choices because of higher confidence in the efficacy. Further, the pre-selection of patients who are likely to respond well to a medicine, drug, or combination therapy may reduce the number of patients needed in a clinical study or accelerate the time needed to complete a clinical development program.

However, no prognostic and predictive markers have been developed, which can be used to predict patients who respond to a Cdc7 kinase inhibitor.

CITATION LIST

Patent Literature

PTL 1: WO2011/102399 A1

Non Patent Literature

NPL 1: EMBO J. 1999, 18(20), p. 5703-5713
NPL 2: J Cell Physiol. 2002, 190(3), p. 287-296
NPL 3: Oncogene. 2008, 27(24), p. 3475-3482
NPL 4: Neoplasia. 2008, 10(9), p. 920-931
NPL 5: Cancer Res. 2004, 64(19), p. 7110-7116
NPL 6: J Biol Chem. 2007, 282(1), p. 208-215

SUMMARY OF INVENTION

Technical Problem

It is an object of the present invention to provide a predictive marker or markers which can make it possible to identify the likelihood that a patient will respond to a pancreatic cancer treatment with a Cdc7 kinase inhibitor, and to provide therapeutic methods for treating subjects suffering from pancreatic cancer with a Cdc7 kinase inhibitor.

Solution to Problem

The present inventors have found that a pancreatic cancer having KRAS gene mutation(s) responds well to the Cdc7 kinase inhibitor, 2-[(2S)-1-azabicyclo[2.2.2]oct-2-yl]-6-(3-methyl-1H-pyrazol-4-yl)thieno[3,2-d]pyrimidin-4(3H)-one (Compound 1) having the chemical structure:

[Chem.2]

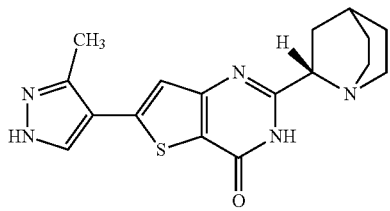

and/or tautomers thereof or a pharmaceutically acceptable salt or hydrate thereof as compared to a pancreatic cancer with no KRAS gene mutation. The present inventors have conducted further studies and completed the present invention. Accordingly, the present invention relates to the following.

1. A method of predicting the likelihood that a patient will respond therapeutically to a pancreatic cancer treatment comprising the administration of 2-[(2S)-1-azabicyclo[2.2.2]oct-2-yl]-6-(3-methyl-1H-pyrazol-4-yl)thieno[3,2-d]pyrimidin-4(3H)-one (Compound 1) and/or tautomers thereof or a pharmaceutically acceptable salt or hydrate thereof, wherein Compound 1 has the structure:

[Chem.3]

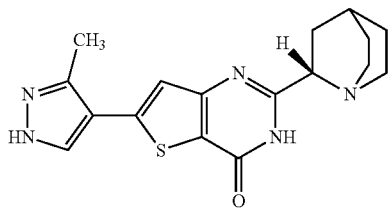

comprising the steps of:
STEP (1): determining a KRAS gene mutation status of a sample from a patient, and
STEP (2): predicting an increased likelihood that the patient will respond therapeutically to the pancreatic cancer treatment if the patient has the presence of KRAS gene mutation(s), 2. A method of treating a patient with a pancreatic cancer comprising the steps of: STEP (1): determining a KRAS gene mutation status of a sample from a patient, STEP (2): identifying 2-[(2S)-1-azabicyclo[2.2.2]oct-2-yl]-6-(3-methyl-1H-pyrazol-4-yl)thieno[3,2-d]pyrimidin-4(3H)-one (Compound 1) and/or tautomers thereof or a pharmaceutically acceptable salt or hydrate thereof, wherein Compound 1 has the structure:

[Chem.4]

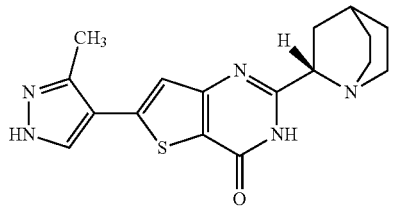

as a therapeutic agent to be administered to the patient if the patient has the presence of KRAS gene mutation(s), and
STEP (3): administering to the patient a therapeutically effective amount of Compound 1 and/or tautomers thereof or a pharmaceutically acceptable salt or hydrate thereof, 3. A method of treating a patient with a pancreatic cancer by improving a likelihood that the patient will respond therapeutically to a pancreatic cancer treatment comprising the administration of 2-[(2S)-1-azabicyclo[2.2.2]oct-2-yl]-6-(3-methyl-1H-pyrazol-4-yl)thieno[3,2-d]pyrimidin-4(3H)-one (Compound 1) and/or tautomers thereof or a pharmaceutically acceptable salt or hydrate thereof, wherein Compound 1 has the structure:

[Chem.5]

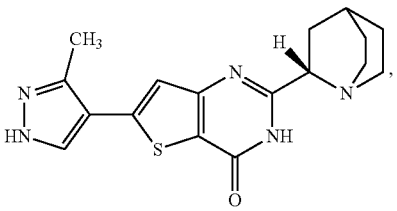

comprising the steps of:
STEP (1): determining a KRAS gene mutation status of a sample from a patient,
STEP (2-1): predicting a not improved likelihood that the patient will respond therapeutically to the pancreatic cancer treatment, if the patient's KRAS gene mutation status is wild type KRAS, and
excluding the patient from a patient group to be administered Compound 1 and/or tautomers thereof or a pharmaceutically acceptable salt or hydrate thereof,
STEP (2-2): predicting an increased likelihood that the patient will respond therapeutically to the pancreatic cancer treatment, if the patient's KRAS gene mutation status is not wild type KRAS, and
administering Compound 1 and/or tautomers thereof or a pharmaceutically acceptable salt or hydrate thereof to the patient,
4. The method of 1., which further comprises the steps of:
STEP (1'): determining a Tp53 and/or p16Ink4 gene mutation status of the sample from the patient, and
STEP (2'): predicting a further increased likelihood that the patient will respond therapeutically to the pancreatic cancer treatment if the patient has the presence of Tp53 and/or p16Ink4 gene mutation(s) in combination with KRAS gene mutation(s),
5. The method of 2. or 3., which comprises the steps of:
STEP (1'): determining a Tp53 and/or p16Ink4 gene mutation status of the sample from the patient, STEP (2') or STEP (2-2'): predicting a further increased likelihood that the patient will respond therapeutically to the pancreatic cancer treatment, if the patient has the presence of Tp53 and/or p16Ink4 gene mutation(s) in combination with KRAS gene mutation(s).

3'. A method of treating a patient with a pancreatic cancer by improving a likelihood that the patient will respond therapeutically to a pancreatic cancer treatment, comprising the steps of:

STEP (1): determining a KRAS gene mutation status of a sample from a patient,

STEP (2): predicting that administration of 2-[(2S)-1-azabicyclo[2.2.2]oct-2-yl]-6-(3-methyl-1H-pyrazol-4-yl)thieno[3,2-d]pyrimi din-4(3H)-one (Compound 1) and/or tautomers thereof or a pharmaceutically acceptable salt or hydrate thereof, wherein Compound 1 has the structure:

[Chem.6]

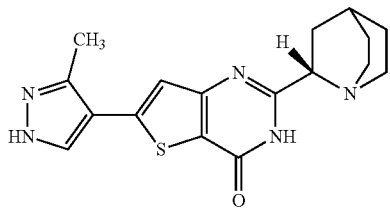

will not improve the likelihood that the patient will respond therapeutically to the pancreatic cancer treatment, if the patient's KRAS gene mutation status is wild type KRAS, STEP (3): excluding the patient for whom it is predicted that administration of Compound 1 and/or tautomers thereof or a pharmaceutically acceptable salt or hydrate thereof will not improve the likelihood that the patient will respond therapeutically to the pancreatic cancer treatment from a patient group to be administered Compound 1 and/or tautomers thereof or a pharmaceutically acceptable salt or hydrate thereof, STEP (4): administering Compound 1 and/or tautomers thereof or a pharmaceutically acceptable salt or hydrate thereof to the patient with a KRAS gene mutation status that is not wild type KRAS.

5'. The method of 2., 3. or 3'., which comprises the steps of:

STEP (1'): determining a Tp53 and/or p16Ink4 gene mutation status of the sample from the patient, STEP (2') or STEP (2-2'): predicting that administration of Compound 1 and/or tautomers thereof or a pharmaceutically acceptable salt or hydrate thereof will not improve the likelihood that the patient will respond therapeutically to the pancreatic cancer treatment, if the patient's Tp53 and/or p16Ink4 gene mutation status is wild type Tp53 and/or p16Ink4 in combination with the patient's KRAS gene mutation status is wild type KRAS, STEP (4'): administering Compound 1 and/or tautomers thereof or apharmaceutically acceptable salt or hydrate thereof to the patient with a Tp53 and/or p16Ink4 gene mutation status is not wild type Tp53 and/or p16Ink4.

The determination of a gene mutation status including KRAS gene mutation status may be performed using methods well known in the art, for example, by an in vitro method in which a step of determining the gene mutation status in the patient comprises taking a sample from the patient and then determining the gene mutation status of the sample. The sample may comprise, for example, at least one of serum, whole fresh blood, peripheral blood mononuclear cells, frozen whole blood, fresh plasma, frozen plasma, urine, saliva, skin, hair follicle, bone marrow, tumor tissue, tumor biopsy, or archived paraffin-embedded tumor tissue.

The status of a gene mutation including the KRAS gene mutation may be, for example, at the level of genomic DNA, protein and/or mRNA transcript of KRAS gene.

The determination of any gene mutation described herein, including the KRAS gene mutation may be performed using a method selected from the group comprising: (a) PCR; (b) RT-PCR; (c) FISH; (d) IHC; (e) immunodetection methods; (f) Western Blot; (g) ELISA; (h) radioimmuno assays; (i) immunoprecipitation; (j) FACS (k) HPLC; (l) surface plasmon resonance; (m) optical spectroscopy; and (n) mass spectrometry. Presence of KRAS gene mutation(s) can be further detected by any sequencing method, including dideoxy sequencing, pyrosequencing, PYROMARK (registered trademark), KRAS assays, and allele-specific PCR assay.

The determination of the KRAS gene may be detected using kits known in the art, for example, RASKET kit (Trade name, MEBGEN).

The present invention also provides a diagnostic reagent kit which may be useful for predicting a likelihood that a patient will respond therapeutically to a pancreatic cancer treatment comprising the administration of Compound 1 and/or tautomers thereof or a pharmaceutically acceptable salt or hydrate thereof, comprising a component for determining KRAS gene mutation status. Said kit may further comprise a component for determining the mutation status of Tp53 and/or p16Ink4 gene. Said kit can further comprise instructions for determining the mutation status of the KRAS, Tp53 and/or p16Ink4 gene mutation(s).

The present invention also provides a kit which may be useful for treating a patient with pancreatic cancer comprising: (a) a component for determining KRAS gene mutation status; and (b) a therapeutically effective amount of Compound 1 and/or tautomers thereof or a pharmaceutically acceptable salt or hydrate thereof. Said kit may further comprise instructions to administer Compound 1 and/or tautomers thereof or a pharmaceutically acceptable salt or hydrate thereof to the patient if KRAS gene mutation(s) is presented in the patient. Said kit may further comprise a component for determining the mutation status of Tp53 and/or p16Ink4 gene for pancreatic cancer.

The present invention also provides a method for treating a pancreatic cancer in a patient in need thereof, comprising administering to the patient a therapeutically effective amount of Compound 1 and/or tautomers thereof or a pharmaceutically acceptable salt or hydrate thereof, wherein the pancreatic cancer comprises KRAS gene mutation(s). In one aspect, the cancer is KRAS mutated pancreatic cancer and the cancer further comprises Tp53 and/or p16Ink4 gene mutation(s).

Advantageous Effects of Invention

By the method of the present invention, accurate prediction of the sensitivity of a patient with a pancreatic cancer to treatment with Compound 1 and/or tautomers thereof or a pharmaceutically acceptable salt or hydrate thereof may be expected. By the method of the present invention, preselection of pancreatic cancer patients who are likely to respond well to Compound 1 and/or tautomers thereof or a pharmaceutically acceptable salt or hydrate thereof may be performed. This increases the chances of successful treatment for the patient and reduces the chances of subjecting the patient to the burden of a treatment that is less likely to be successful, and further promotes improved efficiency in the use of health care resources.

BRIEF DESCRIPTION OF DRAWINGS

FIG. 1 shows in vivo antitumor activity of Compound 1 hemihydrate on KRAS-mutant pancreatic tumors and KRAS-non-mutant (wt) pancreatic tumors.

DESCRIPTION OF EMBODIMENTS

Detailed Description of the Invention

The present invention relates to use of KRAS gene mutation status as a marker for predicting resistance or sensitivity to therapy with a Compound 1 and/or tautomers thereof or a pharmaceutically acceptable salt or hydrate thereof prior to or concurrent with treatment, in addition to methods of treating patients with such resistance or such sensitivity and the treatment regimens related thereto.

Specifically, the present inventors carried out in vitro and in vivo studies with a Cdc7 kinase inhibitor, 2-[(2S)-1-azabicyclo[2.2.2]oct-2-yl]-6-(3-methyl-1H-pyrazol-4-yl)thieno[3,2-d]pyrimi din-4(3H)-one (Compound 1) and/or tautomers thereof or a pharmaceutically acceptable salt or hydrate thereof, and found that pancreatic cancers with KRAS gene mutation(s) may be more sensitive to Compound 1 and/or tautomers thereof or a pharmaceutically acceptable salt or hydrate thereof as compared to pancreatic cancers with no KRAS gene mutation.

In one aspect, the present invention provides a method of predicting the likelihood that a patient will respond therapeutically to a pancreatic cancer treatment comprising the administration of Compound 1 and/or tautomers thereof or a pharmaceutically acceptable salt or hydrate thereof, which comprises determining a KRAS gene mutation status of a sample from a patient.

In one embodiment, the prediction method of the present invention comprises the following steps:

STEP (1): determining a KRAS gene mutation status of a sample from a patient, and STEP (2): predicting an increased likelihood that the patient will respond therapeutically to the pancreatic cancer treatment if the patient has the presence of KRAS gene mutation(s).

In STEP (1), the KRAS gene mutation status of a sample taken from a pancreatic cancer patient is determined.

In this specification, the KRAS gene mutation encompasses the mutation in a single allele and the mutations in both alleles. When the KRAS gene mutations are found in both alleles, the gene mutations in each allele may be the same or different.

The pancreatic cancer may be, for example, pancreatic duct cancer or pancreatic endocrine tumor.

Examples of the sample used in STEP (1) may be a biological sample which includes, but are not limited to, serum, whole fresh blood, peripheral blood mononuclear cells, frozen whole blood, fresh plasma, frozen plasma, urine, saliva, skin, hair follicle, bone marrow, tumor tissue, tumor biopsy, or archived paraffin-embedded tumor tissue. The sample is preferably tumor tissue or tumor biopsy comprising pancreatic cancer cells.

The status of the KRAS gene mutation may be, for example, at the level of genomic DNA, protein and/or mRNA transcript of KRAS gene. Preferably, presence or absence of mutation in KRAS gene is determined at the level of genomic DNA or mRNA transcript.

Methods for determining the gene mutation including KRAS mutation are well known in the art. Examples of such method include, but are not limited to, RFLP (Restriction Fragment Length Polymorphism) method, PCR-SSCP (Single Strand DNA Conformation Polymorphism) method, ASO (Allele Specific Oligonucleotide) hybridization method, sequencing method, ARMS (Amplification Refracting Mutation System) method, denaturing gradient gel electrophoresis method, RNAse A cleavage method, DOL (Dye-labeled Oligonucleotide Ligation) method, TaqMan PCR method, primer extension method, invader method, Scorpion-ARMS method, F-PHFA method, pyrosequence method, BEAMing method, RT-PCR, FISH, IHC, immunodetection method, Western Blot, ELISA, radioimmuno assay, immunoprecipitation, FACS, HPLC, surface plasmon resonance, optical spectroscopy, and mass spectrometry.

While the KRAS gene mutation to be detected in STEP (1) is not particularly limited, it is preferably missense mutation or nonsense mutation. Examples of such KRAS gene mutation include missense mutation or nonsense mutation at codon 5, codon 12, codon 13, codon 14, codon 18, codon 19, codon 23, codon 31, codon 38, codon 59, codon 61, codon 62, codon 97, codon 117, codon 118, codon 119, codon 121, codon 140, codon 143, codon 145, codon 146, codon 151, codon 153, codon 168, codon 171, codon 180, codon 185, codon 187, codon 188 of KRAS gene. More specific examples thereof include, but are not limited to, p.Y5N, p.G12A, p.G12C, p.G12D, p.G12R, p.G12S, p.G12V, p.G13C, p.G13D, p.V14I, p.A18N, p.L19F, p.L23R, p.Q31*, p.D38N, p.A59G, p.A59T, p.Q61H, p.Q61K, p.E62Y, p.Q61L, p.R97I, p.K117N, p.M118V, p.D119N, p.P121H, p.P140H, p.D143G, p.S145L, p.A146T, p.G151A, p.D153V, p.E168fs, p.I171M, p.K180del, p.K185fs, p.I187V, p.M188V and the like. The status of KRAS mutation (preferably missense mutation or nonsense mutation) at codon 12 is preferably detected. More specific examples of the KRAS mutation at codon 12 include, but are not limited to, p.G12A, p.G12C, p.G12D, p.G12R, p.G12S, p.G12V and the like.

As shown in the Examples, pancreatic cancers with KRAS gene mutation(s) may be expected to be more sensitive to Compound 1 and/or tautomers thereof or a pharmaceutically acceptable salt or hydrate thereof as compared to pancreatic cancers with no KRAS gene mutation. Based on these results, if the presence of at least one of KRAS gene mutation is detected in the patient (in a sample from a pancreatic cancer patient) (i.e., in the case of KRAS mutant), an increased likelihood that the patient and the pancreatic cancer in the patient will respond therapeutically to the pancreatic cancer treatment with Compound 1 and/or tautomers thereof or a pharmaceutically acceptable salt or hydrate thereof may be predicted (i.e., it may be predicted that the patient and the pancreatic cancer in the patient is likely to respond therapeutically well to the pancreatic cancer treatment with Compound 1 and/or tautomers thereof or a pharmaceutically acceptable salt or hydrate thereof). If the presence of a KRAS gene mutation is not detected in the patient (in a sample from a pancreatic cancer patient) (i.e., in the case of KRAS non-mutant(wild type KRAS)), the likelihood that the patient and the pancreatic cancer in the patient will not respond therapeutically to the treatment with Compound 1 and/or tautomers thereof or a pharmaceutically acceptable salt or hydrate thereof may be predicted (i.e., it may be predicted that the patient and the pancreatic cancer in the patient is not likely to respond therapeutically well to the pancreatic cancer treatment with Compound 1 and/or tautomers thereof or a pharmaceutically acceptable salt or hydrate thereof).

A patient with a pancreatic cancer may be treated by administering a therapeutically effective amount of Compound 1 and/or tautomers thereof or a pharmaceutically acceptable salt or hydrate thereof, if said patient is predicted, according to the above-mentioned prediction method of the present invention, to have an increased likelihood of response therapeutically to a pancreatic cancer treatment comprising the administration of Compound 1 and/or tautomers thereof or a pharmaceutically acceptable salt or hydrate thereof (i.e., if it is predicted that the patient and the pancreatic cancer in the patient are likely to respond therapeutically well to the pancreatic cancer treatment with Compound 1 and/or tautomers thereof or a pharmaceutically acceptable salt or hydrate thereof) (that is, at least one KRAS gene mutation (KRAS mutant) is detected in the pancreatic cancer patient). In the aforementioned prediction method of the present invention, if a patient is not predicted to have an improved likelihood of therapeutic response to Compound 1 and/or tautomers thereof or a pharmaceutically acceptable salt by the administration of Compound 1 and/or tautomers thereof or a pharmaceutically acceptable salt or hydrate thereof (i.e., if it is predicted that the patient and the pancreatic cancer in the patient are not likely to respond therapeutically well to the pancreatic cancer treatment with Compound 1 and/or tautomers thereof or a pharmaceutically acceptable salt or hydrate thereof) (that is, KRAS gene mutation is not detected in the patient, KRAS non-mutant (wild type KRAS)), said patient may be removed from the administration subject cancer patient group, and Compound 1 and/or tautomers thereof or a pharmaceutically acceptable salt or hydrate thereof may be administered to pancreatic cancer patients predicted to have an increased likelihood that the patient will respond therapeutically to a pancreatic cancer treatment comprising the administration of Compound 1 and/or tautomers thereof or a pharmaceutically acceptable salt or hydrate thereof (that is, pancreatic cancer patients in which at least one KRAS gene mutation (KRAS mutant) is detected), whereby the patient with the KRAS mutant pancreatic cancer may be treated with higher reliability. The present invention also provides a treatment method of such pancreatic cancer patients. Pancreatic cancer patients may be treated more certainly by removing pancreatic cancer patients highly likely to be low responders from the administration subject group, selecting pancreatic cancer patients more likely to be high responders, and administering Compound 1 and/or tautomers thereof or a pharmaceutically acceptable salt or hydrate thereof to the pancreatic cancer patients likely to be high responders.

In one aspect, the prediction method of the present invention may further comprise a step of determining a Tp53 and/or p16Ink4 gene mutation status of the sample from the patient. Examples of the sample for the determination of Tp53 and/or p16Ink4 include the sample used in STEP (1) and the like.

In this aspect, if the presence of Tp53 and/or p16Ink4 gene mutation(s) is detected in the patient (in a sample from the cancer patient), in addition to KRAS gene mutation(s), it may be predicted that there is a further increased likelihood the patient and the pancreatic cancer in the patient will respond therapeutically to the treatment with Compound 1 and/or tautomers thereof or a pharmaceutically acceptable salt or hydrate thereof (i.e., it may be predicted that the patient and the pancreatic cancer in the patient are further likely to respond therapeutically well to the pancreatic cancer treatment with Compound 1 and/or tautomers thereof or a pharmaceutically acceptable salt or hydrate thereof).

Compound 1 has the following chemical structure:

[Chem.7]

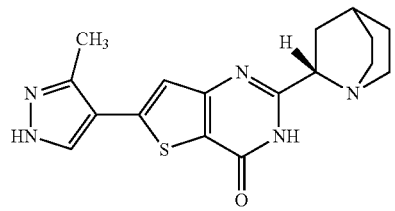

Tautomers of Compound 1 or a pharmaceutically acceptable salt or hydrate of Compound 1 are/is also encompassed in the present invention. When Compound 1 has a tautomer, each isomer is also encompassed in the present invention.

Compound 1 and/or tautomers thereof can be used in the form of pharmaceutically acceptable salt. Examples of the pharmaceutically acceptable salt include salts with inorganic bases, salts with organic bases, salts with inorganic acids, salts with organic acids, and salts with basic or acidic amino acids.

Compound 1 and/or tautomers thereof may be a hydrate (e.g., hemihydrate), a non-hydrate, a solvate or a non-solvate, all of which are encompassed in the present invention.

Compound 1 and/or tautomers thereof or a pharmaceutically acceptable salt or hydrate thereof or a crystal form thereof can be obtained according to the production methods described in PCT Publication No. WO 2011/102399, U.S. Pat. Nos. 8,722,660, 8,921,354, 8,933,069, U.S. Patent Publication No. US 2015/158882, U.S. provisional application No. 62/314,080, filed on Mar. 28, 2016, and U.S. provisional application No. 62/367,842, filed on Jul. 28, 2016, which are incorporated herein by reference in their entirety and for all purposes, or a method analogous thereto.

An isomer of Compound 1 (such as an optical isomer, a stereoisomer, a regioisomer, a rotamer and the like) and a mixture thereof are also encompassed in the present invention. For example, when Compound 1 has an optical isomer, an optical isomer resolved from a racemate is also encompassed in the present invention. These isomers can be obtained as single products by synthetic techniques and separation techniques known per se (e.g., concentration, solvent extraction, column chromatography, recrystallization).

Compound 1 and/or tautomers thereof or a pharmaceutically acceptable salt or hydrate thereof may be in the form of a crystal (e.g., crystalline form A, crystalline form I etc.), and the crystal form of the crystal may be single or plural, both of which are encompassed in Compound 1. The crystal can be produced by the method described in U.S. provisional application No. 62/314,080, filed on Mar. 28, 2016, U.S. provisional application No. 62/367,842, filed on Jul. 28, 2016 and/or by reference examples 1 and 2 herein.

Compound 1 and/or tautomers thereof or a pharmaceutically acceptable salt or hydrate thereof may be administered, as a medicament, orally or parenterally as it is or in a mixture with a pharmaceutically acceptable carrier to the aforementioned patient.

The medicament comprising Compound 1 and/or tautomers thereof or a pharmaceutically acceptable salt or hydrate thereof (sometimes to be abbreviated as "the medicament for use in the present invention") is explained in detail in the following.

Examples of the dosage form of the medicament for use in the present invention for oral administration of Compound 1 and/or tautomers thereof or a pharmaceutically acceptable salt or hydrate thereof include oral preparations such as a capsule.

In some embodiments, the medicament for use in the present invention comprises Compound 1 and/or tautomers thereof or a pharmaceutically acceptable salt or hydrate thereof and further comprises a filler. In some embodiments, said filler is mannitol or lactose. In some embodiments, said filler is present in an amount ranging from 49 to 90 wt % of the medicament.

In some embodiments, the medicament for use in the present invention comprises Compound 1 and/or tautomers thereof or a pharmaceutically acceptable salt or hydrate thereof and further comprises a glidant. In some embodiments, said glidant is colloidal silicon dioxide. In some embodiments, said glidant is present in an amount ranging from 1 to 4 wt % of the medicament.

In some embodiments, the medicament for use in the present invention comprises a mixture of Compound 1 and/or tautomers thereof or a pharmaceutically acceptable salt or hydrate thereof.

In some embodiments, the medicament for use in the present invention comprises Compound 1 and/or tautomers thereof or a pharmaceutically acceptable salt or hydrate thereof and at least one filler chosen from mannitol and lactose.

In some embodiments, the medicament for use in the present invention comprises Compound 1 and/or tautomers thereof or a pharmaceutically acceptable salt or hydrate thereof and mannitol, wherein the mannitol is present in an amount ranging from 49 to 90 wt % of the medicament.

In some embodiments, the medicament for use in the present invention comprises Compound 1 and/or tautomers thereof or a pharmaceutically acceptable salt or hydrate thereof and lactose, wherein the lactose is present in an amount ranging from 49 to 90 wt % of the medicament.

In any of the above-mentioned embodiments, the medicament for use in the present invention comprising Compound 1 and/or tautomers thereof or a pharmaceutically acceptable salt or hydrate thereof further comprises colloidal silicon dioxide. In some embodiments, the colloidal silicon dioxide is present in an amount ranging from 1 to 4 wt % of the medicament.

In some embodiments, the medicament comprising Compound 1 and/or tautomers thereof or a pharmaceutically acceptable salt or hydrate thereof is in the form of a capsule. In some embodiments, said capsule further comprises at least one filler and at least one glidant. In some embodiments, said filler is mannitol. In some embodiments, said glidant is colloidal silicon dioxide.

In some embodiments, the medicament comprising Compound 1 and/or tautomers thereof or a pharmaceutically acceptable salt or hydrate thereof in the form of a capsule comprises from 5 to 15 wt % Compound 1 and/or tautomers thereof or a pharmaceutically acceptable salt or hydrate thereof, from 85 to 95 wt % filler, and from 0.5 to 2% glidant relative to the weight of the capsule, excluding the capsule shell. In some embodiments, the filler is mannitol. In some embodiments, the glidant is colloidal silicon dioxide. In some embodiments, the capsule shell comprises from 20 to 30 wt % relative to the total weight of the capsule.

While the amount of Compound 1 and/or tautomers thereof or a pharmaceutically acceptable salt or hydrate thereof in the medicament for use in the present invention varies depending on the form of the medicament, it is generally present in an amount ranging from 0.01 to 99.9 wt %, for example 2 to 85 wt %, such as 5 to 70 wt %, relative to the weight of the entire medicament.

While the amount of the additive in the medicament for use in the present invention varies depending on the form of the medicament, it is generally present in an amount ranging from 1 to 99.9 wt %, for instance 10 to 90 wt %, relative to the weight of the entire medicament.

Compound 1 and/or tautomers thereof or a pharmaceutically acceptable salt or hydrate thereof is stable and has low toxicity, and can be used safely. While the daily dose varies depending on the condition and body weight of the patient, administration route and the like, in the case of, for example, Compound 1 and/or tautomers thereof or a pharmaceutically acceptable salt or hydrate thereof may be administered orally in the form of a medicament described herein to a patient for treatment.

In some embodiments, the medicament for use in the present invention comprises a dose strength of Compound 1 and/or tautomers thereof or a pharmaceutically acceptable salt or hydrate thereof ranging from 10 to 200 mg. For example, in some embodiments, a medicament comprises a dose strength of 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 mg of Compound 1 and/or tautomers thereof or a pharmaceutically acceptable salt or hydrate thereof. In some embodiments, the daily dose administered to an adult (body weight about 60 kg) ranges from 10 to 200 mg. In some embodiments, the daily dose administered to an adult is 30 mg orally once or twice a day.

The present invention also provides a diagnostic reagent for predicting the likelihood that a patient will respond therapeutically to a pancreatic cancer treatment comprising the administration of Compound 1 and/or tautomers thereof or a pharmaceutically acceptable salt or hydrate thereof, which comprises a reagent for detecting at least one KRAS gene mutation status. The diagnostic reagent may be included in a kit as a component for determining the status of mutation(s), and the kit may further comprise instructions for using the diagnostic reagent for determining the status of mutation(s).

Examples of the reagent for detecting at least one KRAS gene mutation status include (1) a nucleic acid probe capable of specifically detecting at least one mutation in a genome or mRNA sequence encoding human KRAS (preferably, ORF in a genome or mRNA sequence encoding human KRAS), or (2) a primer capable of specifically amplifying a region containing at least one mutation in a genome or mRNA sequence encoding human KRAS (preferably, ORF in a genome or mRNA sequence encoding human KRAS) and the like.

While the KRAS gene mutation to be detected is not particularly limited, it is preferably missense mutation or nonsense mutation. Examples of such KRAS gene mutation include missense mutation or nonsense mutation at codon 5, codon 12, codon 13, codon 14, codon 18, codon 19, codon 23, codon 31, codon 38, codon 59, codon 61, codon 62, codon 97, codon 117, codon 118, codon 119, codon 121, codon 140, codon 143, codon 145, codon 146, codon 151, codon 153, codon 168, codon 171, codon 180, codon 185, codon 187, codon 188 of KRAS gene. More specific examples thereof include, but are not limited to, p.Y5N, p.G12A, p.G12C, p.G12D, p.G12R, p.G12S, p.G12V, p.G13C, p.G13D, p.V14I, p.A18N, p.L19F, p.L23R, p.Q31*, p.D38N, p.A59G, p.A59T, p.Q61H, p.Q61K, p.E62Y, p.Q61L, p.R97I, p.K117N, p.M118V, p.D119N, p.P121H, p.P140H, p.D143G, p.S145L, p.A146T, p.G151A, p.D153V, p.E168fs, p.I171M, p.K180del, p.K185fs, p.I187V, p.M188V and the like. The status of KRAS mutation at codon 12 (preferably missense mutation or nonsense mutation) is preferably detected. More specific examples of the KRAS mutation at codon 12 include, but are not limited to, p.G12A, p.G12C, p.G12D, p.G12R, p.G12S, p.G12V and the like.

In the present specification, the "specific detection of KRAS mutation by nucleic acid probe" means that a nucleic acid probe hybridizes to a region containing a particular mutation in a genome or mRNA encoding human KRAS, and does not hybridize to the corresponding wild-type region. The conditions for such hybridization may be appropriately selected by those of ordinary skill in the art. As the hybridization conditions, for example, low stringent conditions may be mentioned. The low stringent conditions are, for example, the conditions of 42° C., 5×SSC, 0.1% SDS, preferably 50° C., 2×SSC, 0.1% SDS conditions, in washing after hybridization. More preferable hybridization conditions include high stringent conditions. The high stringent conditions are, for example, 65° C., 0.1×SSC, 0.1% SDS. The factors that influence the hybridization stringency include plural factors such as temperature, salt concentration and the like, and those of ordinary skill in the art can realize similar stringency by appropriately selecting these factors.

The nucleic acid probe of (1) preferably shows the difference between the affinity for a genome or mRNA encoding human KRAS containing a particular mutation (human KRAS mutant genome or mRNA) targeted by the nucleic acid probe, and the affinity for a genome or mRNA encoding wild type human KRAS free of the mutation (human KRAS wild type genome or mRNA), and hybridizes to a human KRAS mutant genome or mRNA but does not hybridize to a human KRAS wild type genome or mRNA under appropriate conditions (e.g., high stringent conditions).

The nucleic acid probe of (1) is, for example, a polynucleotide containing a continuous partial sequence of human KRAS mutant genome or mRNA sequence (preferably, ORF in human KRAS mutant genome or mRNA sequence) or a complementary sequence of the partial sequence, wherein the partial sequence contains at least one mutation, and the partial sequence or a complementary sequence thereof has a length of at least 8, 10, 12, 14, 16, 18 or 20 nucleotides. Since the genome or mRNA sequence encoding human KRAS is known, and the aforementioned KRAS mutation pointed out to be related to pancreatic cancer is also known, those of ordinary skill in the art can design an appropriate nucleic acid probe for the detection of the KRAS mutation based on these information.

The nucleic acid probe of the above-mentioned (1) may be a DNA or RNA, or a DNA/RNA chimera, preferably a DNA. The nucleic acid may be a double strand or single strand, preferably a single strand.

When the nucleic acid probe contains a complementary sequence of a continuous partial sequence of human KRAS mutant genome or mRNA sequence (preferably, ORF in human KRAS mutant genome or mRNA sequence), the complementarity of the complementary sequence is 80%-100%, preferably 90%-100%, more preferably 100%.

The length of the continuous partial sequence of human KRAS mutant genome or mRNA sequence or a complementary sequence of the partial sequence contained in the nucleic acid probe is not less than 8 nucleotides, preferably not less than 12, 14, 16, 18 or 20 nucleotides (e.g., not less than 25 nucleotides). While the upper limitation of the length of the partial sequence or a complementary sequence thereof is not particularly limited, it is generally not more than 1000 nucleotides, preferably not more than 100 nucleotides, more preferably not more than 50 nucleotides, further preferably not more than 30 nucleotides, from the aspect of easy synthesis and high detection sensitivity of mutation.

The length of the nucleic acid probe is at least not less than 8 nucleotides, preferably not less than 12, 14, 16, 18 or 20 nucleotides. While the upper limit of the length of the polynucleotide of the present invention is not particularly limited, it is generally not more than 1000 nucleotides, preferably not more than 100 nucleotides, more preferably not more than 50 nucleotides, further preferably not more than 30 nucleotides, from the aspect of easy synthesis.

The nucleic acid probe may contain any additional sequence in addition to a continuous partial sequence of human KRAS mutant genome or mRNA sequence (preferably, ORF in human KRAS mutant genome or mRNA sequence) or a complementary sequence of the partial sequence.

In addition, the nucleic acid probe may be labeled with a suitable label, for example, radioisotope (e.g., $^{125}$I, $^{131}$I, $^{3}$H, $^{14}$C, $^{32}$P, $^{33}$P, $^{35}$S etc.), enzyme (e.g., beta-galactosidase, beta-glucosidase, alkaline phosphatase, peroxidase, malic acid dehydrogenase etc.), fluorescent substance (e.g., fluorescamine, fluorescein isothiocyanate etc.), luminescence substance (e.g., luminol, luminol derivative, luciferin, lucigenin etc.), quenching substance and the like.

In the present specification, "specific amplification of mutation by primer" means that a primer set selectively amplifies by PCR a region containing a particular mutation in a DNA comprising a human KRAS mutant genome or mRNA sequence, to a degree distinguishable from other region of human genomic DNA.

The primer of the above-mentioned (2) includes a primer capable of initiating complementary strand synthesis towards the selected mutation by using, as a template, a polynucleotide (e.g., DNA) comprising a human KRAS mutant genome or mRNA sequence and containing a particular KRAS mutation. Said primer can also be expressed as a primer for forming a replication origin at the 3'-side of the mutation site in a polynucleotide containing a KRAS mutation. The distance between the hybridization region of a primer and a mutation site is optional. The distance between them can be any preferable length selected according to the analysis method of the base of the mutation site. For example, as a primer for an analysis by DNA chip or direct sequencing, a primer can be designed to afford an amplification product having a length of generally 25-500, for example, 50-200 nucleotides as a region containing a mutation site. Those of ordinary skill in the art can design a primer suitable for each analysis method, based on the information regarding the KRAS genome or mRNA nucleotide sequence of a peripheral region including a mutation site. The nucleotide sequence constituting the primer of the above-mentioned (2) is not limited to a nucleotide sequence completely complementary to a partial sequence of a human KRAS genome or mRNA sequence or a complementary sequence of the partial sequence, and may be appropriately modified.

The primer of the above-mentioned (2) may be a DNA or RNA, or a DNA/RNA chimera, preferably a DNA. The nucleic acid may be a double strand or single strand, preferably a single strand.

The length of a region in a nucleic acid comprising a human KRAS genome or mRNA sequence or a complementary sequence thereof, to which the primer of the above-mentioned (2) can hybridize, is not less than 12 nucleotides, preferably not less than 15 nucleotides, more preferably not less than 18 nucleotides, further preferably not less than 20 nucleotides (e.g., not less than 25 nucleotides). While the upper limit of the length of the hybridization region is not particularly limited, it is generally not more than 100 nucleotides, preferably not more than 50 nucleotides, more preferably not more than 30 nucleotides, from the aspect of easy synthesis.

The length of the primer of the above-mentioned (2) is at least 12 nucleotides, preferably not less than 15 nucleotides, more preferably not less than 18 nucleotides, further preferably not less than 20 nucleotides. While the upper limit of the length of the polynucleotide of the present invention is not particularly limited, it is generally not more than 100 nucleotides, preferably not more than 50 nucleotides, more preferably not more than 30 nucleotides, from the aspect of easy synthesis.

The primer of the above-mentioned (2) may contain any additional sequence in addition to a continuous partial sequence of human KRAS genome or mRNA sequence, or a complementary sequence of the partial sequence.

The primer may be labeled with a suitable label, for example, radioisotope (e.g., $^{125}$I, $^{131}$I, $^{3}$H, $^{14}$C, $^{32}$P, $^{33}$P, $^{35}$S etc.), enzyme (e.g., beta-galactosidase, beta-glucosidase, alkaline phosphatase, peroxidase, malic acid dehydrogenase etc.), fluorescent substance (e.g., fluorescamine, fluorescein isothiocyanate etc.), luminescence substance (e.g., luminol, luminol derivative, luciferin, lucigenin etc.), quenching substance and the like.

The diagnostic reagent of the present invention may be combined with various enzymes, enzyme substrates, buffers and the like according to the detection method of the KRAS mutation status. Examples of the enzyme include enzymes necessary for various analysis methods exemplified as the detection method of the above-mentioned mutation, such as DNA polymerase, DNA ligase, restriction enzyme and the like. As the buffer, a buffer preferable for the maintenance of the activity of enzyme used for the analyses is appropriately selected. As the enzyme substrate, for example, a substrate for complementary chain synthesis and the like are used.

The diagnostic reagent of the present invention may further comprise means for determining the mutation status of Tp53 and/or p16Ink4 gene.

Using the diagnostic reagent of the present invention, the likelihood that a patient will respond therapeutically to a pancreatic cancer treatment comprising the administration of Compound 1 and/or tautomers thereof or a pharmaceutically acceptable salt or hydrate thereof may be easily predicted according to the prediction method of the present invention.

The present invention also provides a kit for use in treating a patient with a pancreatic cancer, comprising the above-mentioned diagnostic reagent of the present invention and a therapeutically effective amount of Compound 1 and/or tautomers thereof or a pharmaceutically acceptable salt or hydrate thereof. Compound 1 and/or tautomers thereof or a pharmaceutically acceptable salt or hydrate thereof may be provided as a medicament or a pharmaceutical composition comprising a therapeutically effective amount of Compound 1 and/or tautomers thereof or a pharmaceutically acceptable salt or hydrate thereof.

The kit of the present invention may further comprise instructions to administer Compound 1 and/or tautomers thereof or a pharmaceutically acceptable salt or hydrate thereof to the patient if KRAS gene mutation is present in the patient.

Using the kit of the present invention, a patient with a pancreatic cancer having an increased likelihood that the patient will respond therapeutically to a pancreatic cancer treatment comprising the administration of Compound 1 and/or tautomers thereof or a pharmaceutically acceptable salt or hydrate thereof (i.e., a patient with a pancreatic cancer who is predicted to be likely to respond therapeutically well to the pancreatic cancer treatment with Compound 1 and/or tautomers thereof or a pharmaceutically acceptable salt or hydrate thereof)(that is, pancreatic cancer patients detected to have at least one of KRAS gene mutations, KRAS mutant) may be easily selected and treated by administering a therapeutically effective amount of Compound 1 and/or tautomers thereof or a pharmaceutically acceptable salt or hydrate thereof to cancer patients predicted, according to the above-mentioned prediction method of the present invention.

EXAMPLES

The present invention is explained in more detail in the following by referring to Examples, Experimental Examples and Formulation Examples, which are not to be construed as limitative, and the invention may be changed within the scope of the present invention.

In the following Examples, the "room temperature" generally shows about 10° C. to about 35° C. The ratios for mixed solvents show, unless otherwise specified, volume mixing ratios. Unless otherwise specified, % shows wt %.

In silica gel column chromatography, basic silica gel column chromatography means use of aminopropylsilane-bound silica gel. $^{1}$H-NMR (proton nuclear magnetic resonance spectrum) was measured by Fourier transform NMR. Very mild peaks of protons in hydroxyl group, an amino group and the like are not described.

The abbreviations in the Examples and Experimental Examples follow general examples currently used in this technical field and mean, for example, the following.

s: singlet
d: doublet
t: triplet
m: multiplet
brs: broad singlet
J: coupling constant
DMSO: dimethyl sulfoxide
Hz: hertz
$^{1}$H-NMR: proton nuclear magnetic resonance
SDS: sodium dodecyl sulfate Reference Example 1

Preparation of Compound 1 Hemihydrate Crystalline Form a Using DMSO/Ethanol/Water 2-[(2S)-1-azabicyclo[2.2.2]oct-2-yl]-6-(3-methyl-1H-pyrazol-4-yl)thieno[3,2-d]pyri midin-4(3H)-one (Crude Compound 1) was obtained according to the method described in Example 178 U.S. Pat. No. 8,722,660 B2. Crude Compound 1 (300 g) was suspended in DMSO (1560 mL) and ethanol (930 mL). The suspension then was dissolved by heating to 75° C. to 85° C. After confirmation of dissolution, dust removal filtration was carried out, and the residue was washed with a mixed solution of DMSO (1040 mL) and ethanol (620 mL). The filtrate and washing solution after the dust removal filtration were combined and stirred at 75° C. to 85° C. After confirmation of no precipitation, water (5580 mL) was added dropwise for 1 hr or longer at the same temperature. After dropwise addition, the mixture was stirred at the same temperature for 1 hr or longer. After confirmation of the precipitation of the crystals, the mixture was allowed to cool to 20° C. to 30° C. and stirred for 2 hrs or longer. After stirring, the crystals were collected by filtration and washed with water (3000 mL) and acetone (1500 mL) successively to give wet crystals. The obtained wet crystals were dried under reduced pressure at 60° C. to give Compound 1 as crystals (Compound 1 hemihydrate Crystalline Form A, 207.3 g, yield 69.1%). The obtained Compound 1 hemihydrate Crystalline Form A crystals (193.3 g) were pulverized in a Jet Mill to give a crystalline powder (pulverized product, form A crystal, 188.9 g). The obtained crystals contained 2.5% water and were characterized by a XRPD pattern with specific peaks at d values (or d-spacings) of 21.5, 10.9, 7.3, 5.4, 5.0, 4.9, 4.5, 3.7, 3.4, 3.3 and 3.0 angstrom.

$^1$H-NMR (600 MHz, DMSO-$d_6$) δ 1.39-1.48 (m, 2H), 1.48-1.58 (m, 2H), 1.75 (t, J=11.1 Hz, 1H), 1.87 (br s, 1H), 2.24-2.36 (m, 1H), 2.46 (s, 3H), 2.53-2.65 (m, 2H), 2.80-2.97 (m, 1H), 3.07 (t, J=11.3 Hz, 1H), 3.91 (t, J=8.9 Hz, 1H), 7.44 (s, 1H), 8.04 (br s, 1H).

Analytical Calculated for C17H19N5O1.5S: C, 58.27; H, 5.75; N, 19.98; 0, 6.85; S, 9.15. Experimental: C, 58.22; H, 5.80; N, 20.03; S, 9.09.

X-ray powder diffraction patterns were collected using a Rigaku Ultima IV(Rigaku, Tokyo, Japan) with Cu-Kα radiation generated at 50 mA and 40 kV. A sample was placed on a silicon plate at room temperature. Data were collected from 2° to 35° (2θ) at a step size of 0.02° and a scanning speed of 6°/min.

Reference Example 2

Preparation of Compound 1 Hemihydrate Crystalline Form I Using DMSO/Acetone/Water 2-[(2S)-1-azabicyclo[2.2.2]oct-2-yl]-6-(3-methyl-1H-pyrazol-4-yl)thieno[3,2-d]pyrimidin-4(3H)-one (Crude Compound 1) was obtained according to the method described in Example 178 of U.S. Pat. No. 8,722,660 B2. Crude Compound 1 (30 g) was dissolved in DMSO (300 mL) at 20° C. to 30° C. After confirmation of dissolution, dust removal filtration was carried out and a filtrate solution was obtained. The residue was washed with DMSO (60 mL), and a washing solution was obtained. A mixed solution of acetone (150 mL) and water (150 mL) was stirred at 45° C. to 55° C., and 45 mL of the filtrate solution was added dropwise for 10 to 30 min at the same temperature. After dropwise addition, the mixture was stirred at the same temperature for 10 min. To the mixture, 15 mL of the filtrate solution was added dropwise for 3 to 10 min at the same temperature. After dropwise addition, the mixture was stirred at the same temperature for 1 hr or longer. After confirmation of the precipitation of the crystals, the rest of the filtrate solution was added dropwise for 1 to 2 hr at the same temperature. After dropwise addition, the washing solution was added dropwise at the same temperature. After dropwise addition, the mixture was stirred at the same temperature for 1 hr. After stirring, the mixture was allowed to cool to 20° C. to 30° C. and stirred for 1 hr or longer. After stirring, the crystals were collected by filtration and washed with water (150 mL) and acetone (150 mL) successively to give wet crystals. The obtained wet crystals were dried under reduced pressure at 60° C. to give Compound 1 as crystals (Compound 1 hemihydrate Crystalline Form I, 25.9 g, yield 86.3%).

Example 1

In Vivo Antitumor Activity of Compound 1 Hemihydrate in Female BALB/c Nude Mice Bearing Patient-Derived Tumor Xenografts (PDXs)

Materials and Methods

PDX Models

The PDX models at CrownBio international R&D center (Crown Bioscience, Inc., Beijing, China) were used for in vivo efficacy studies of Compound 1 hemihydrate. The PDX models include 25 pancreatic models including PA0787, PA1168, PA1338, PA1383, PA1644, PA3013, PA3065, PA3126, PA1170, PA1357, PA3137, PA1194, PA1198, PA1280, PA1301, PA1306, PA1390, PA1405, PA1459, PA3060, PA6237, PA6238, PA6258, PA6259, and PA6262.

Efficacy Studies

Tumor fragments from seed mice inoculated with selected PDX tumors were harvested and used for inoculation into BALB/c nude mice. Each mouse was inoculated subcutaneously at the right flank with one tumor fragment (2-3 mm in diameter). The treatments were started when mean tumor size reached approximately 200-250 mm$^3$. For each model, 6 tumor bearing mice were randomized into 2 groups. Mice were dosed orally with either vehicle (0.5% w:v methyl cellulose) or Compound 1 hemihydrate Form A crystal (60 mg/kg, Bid, po, 21 days, 3 days on 4 days off).

The % tumor growth inhibition (TGI) was taken as endpoints to determine when the tumor growth can be delayed or mice can be cured. Tumor sizes were measured twice weekly in two dimensions using a caliper, and the volume is expressed in mm$^3$ using the formula:

$$V = 0.5 a \times b^2,$$

where a and b are the long and short diameters of the tumor, respectively. The % TGI was calculated using the following formula:

$$\% \text{ TGI} = (1 - (Ti - T0)/(Vi - V0)) * 100$$

Ti as the arithmetic mean tumor volume of the treatment group on the measurement day; T0 as the arithmetic mean tumor volume of the treatment group at Day0; Vi as the arithmetic mean tumor volume of control group at the measurement day; V0 as the arithmetic mean tumor volume of the control group at Day0.

Statistics

Mutation data of KRAS in each PDX model were obtained from the database of Crown Bioscience, Inc. The statistical analysis was performed on % TGI of Compound 1 treatment using a Student's t-test between KRAS-mutant PDX models and KRAS-wild PDX models. Differences were considered significant at p≤0.05.

Results and Conclusions

Compound 1 hemihydrate exhibited significant antitumor efficacy (>60% tumor growth inhibition) in pancreatic models (22 out of 25) including PA0787, PA1168, PA1338, PA1383, PA1644, PA3013, PA3065, PA3126, PA1170, PA1357, PA3137, PA1194, PA1198, PA1280, PA1301, PA1306, PA1390, PA1405, PA1459, PA3060, PA6237, PA6238, PA6258, PA6259, and PA6262 PDX models. A correlative study revealed that the KRAS-mutant pancreatic tumors were more sensitive to Compound 1 hemihydrate compared to the KRAS-wild type ones (FIG. 1). Based on these results, Compound 1 hemihydrate may be expected to be more effective for KRAS mutant tumors.

Example 2

Testing Compound 1 in Mice

To understand effect of Compound 1 in a KRAS mutated pancreatic cancer in vivo, Compound 1 and/or tautomers thereof or a pharmaceutically acceptable salt or hydrate is/are administered to mice models. Mice models are described in Curry. 2013. Cancer Discov; 3(8) 908-21; Kissil. 2007. Cancer Res 67(17): 8089-8094; Sanchez-Rivera. 2014. Nature. 516: 428-441; Shaw. 2007. Genes and Development. 21:694-707; US20150150892 (A1); Tuveson. 2006. Cancer Res. 66:(1) 242-247; Hingorani. 2003. Cancer Cell. 4: 437-450; Friedlander. 2009. Cancer Cell. 16: 379-389; Cheung. 2010. Oncogene. 29(12): 1857-1864. Mice are treated with Compound 1 and/or tautomers thereof or a pharmaceutically acceptable salt or hydrate. Individual pancreatic tumors are monitored using micro-computed tomography (microCT) imaging prior to treatment and post treatment. To analyze the long-term effects of treatment with Compound 1 and/or tautomers thereof or a pharmaceutically acceptable salt or hydrate, an investigation is performed as to whether a multi-dose regimen of Compound 1 and/or tautomers thereof or a pharmaceutically acceptable salt or hydrate can prolong survival of tumor-bearing mice. Using a cohort of mice (models described above), the tumor-bearing animals are treated once weekly for 4 weeks and survival is monitored.

INDUSTRIAL APPLICABILITY

By the method of the present invention, accurate prediction of the sensitivity of the patient with a pancreatic cancer to treatment with Compound 1 and/or tautomers thereof or a pharmaceutically acceptable salt or hydrate thereof may be expected. By the method of the present invention, preselection of patients who are likely to respond well to Compound 1 and/or tautomers thereof or a pharmaceutically acceptable salt or hydrate is expected to be performed.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claims.

We claim:

1. A method of treating a patient with a pancreatic cancer comprising administering to the patient a therapeutically effective amount of Compound 1

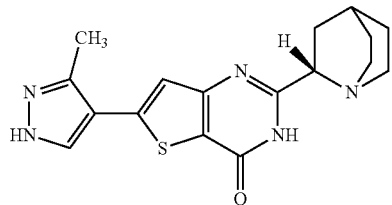

Compound 1 and/or tautomers thereof or a pharmaceutically acceptable salt or hydrate thereof;

wherein the patient has been determined to have a KRAS gene mutation(s) and Tp53 and/or p16Jnk4 gene mutation status.

2. A method of treating a patient with a pancreatic cancer comprising the steps of:

STEP (1): determining a KRAS gene mutation status of a sample from a patient,

STEP (2-1): predicting a likelihood that the patient will not respond therapeutically to the pancreatic cancer treatment, if the patient's KRAS gene mutation status is wild type KRAS; and excluding the patient from a patient group to be administered Compound 1 and/or tautomers thereof or a pharmaceutically acceptable salt or hydrate thereof, STEP (2-2): predicting a likelihood that the patient will respond therapeutically to the pancreatic cancer treatment, if the patient's KRAS gene mutation status is selected from the group consisting of p.Y5N, p.G12A, p.G12C, p.G12D, p.G12R, p.G12S, p.G12V, p.G13C, p.G13D, p.V14I, p.A18N, p.L19F, p.L23R, p.Q31*, p.D38N, p.A59G, p.A59T, p.Q61H, p.Q61K, p.E62Y, p.Q61L, p.R97I, p.K117N, p.M118V, p.D119N, p.P121H, p.P140H, p.D143G, p.S145L, p.A146T, p.G151A, p.D153V, p.E168fs, p.I171M, p.K180del, p.K185fs, p.I187V, p.M188V, and combinations thereof; and administering Compound 1 and/or tautomers thereof or a pharmaceutically acceptable salt or hydrate thereof to the patient

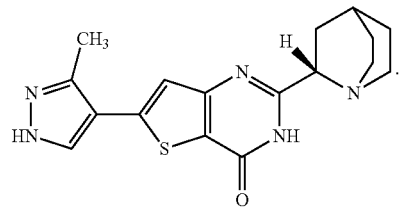

Compound 1

3. The method according to claim 2, which comprises the steps of:

STEP (1'): determining a Tp53 and/or p16Ink4 gene mutation status of the sample from the patient, STEP (2') or STEP (2-2'): predicting a likelihood that the patient will respond therapeutically to the pancreatic cancer treatment, if the patient has the presence of Tp53 and/or p16Ink4 gene mutation(s) in combination with KRAS gene mutation(s).

* * * * *